United States Patent
Brule et al.

(10) Patent No.: US 10,161,846 B2
(45) Date of Patent: Dec. 25, 2018

(54) METHOD OF MODELING PERMEATION TO ESSENCES OF A MULTILAYER POLYMER STRUCTURE

(71) Applicants: ARKEMA FRANCE, Colombes (FR); CENTRE NATIONAL DE LA RECHERCHE SCIENTIFIQUE, Paris (FR); UNIVERSITE DE LORRAINE, Nancy (FR)

(72) Inventors: Benoît Brule, Beaumont le Roger (FR); Jing Zhao, Courbevioe (FR); Anne Jonquieres, Vandoeuvre (FR); Robert Clement, Richardmenil (FR)

(73) Assignee: ARKEMA FRANCE, Colombes (FR)

( * ) Notice: Subject to any disclaimer, the term of this patent is extended or adjusted under 35 U.S.C. 154(b) by 234 days.

(21) Appl. No.: 14/376,954

(22) PCT Filed: Feb. 4, 2013

(86) PCT No.: PCT/FR2013/050229
§ 371 (c)(1),
(2) Date: Aug. 6, 2014

(87) PCT Pub. No.: WO2013/117845
PCT Pub. Date: Aug. 15, 2013

(65) Prior Publication Data
US 2015/0000379 A1    Jan. 1, 2015

(30) Foreign Application Priority Data

Feb. 6, 2012  (FR) ..................... 12 51083

(51) Int. Cl.
*G01N 15/08*  (2006.01)
*B01D 65/10*  (2006.01)
(Continued)

(52) U.S. Cl.
CPC .......... *G01N 15/082* (2013.01); *B01D 65/10* (2013.01); *B01D 69/12* (2013.01); *B01D 71/26* (2013.01);
(Continued)

(58) Field of Classification Search
CPC .................. G01N 15/0826; G01N 15/082
See application file for complete search history.

(56) References Cited

U.S. PATENT DOCUMENTS 5,643,997 A     7/1997  Matsuoka et al.
5,698,303 A *  12/1997  Caldwell ................. A61L 15/26
                                                                    428/215

(Continued)

FOREIGN PATENT DOCUMENTS

CA       2 509 518 A1    12/2005
CN         1315250 A     10/2001
(Continued)

OTHER PUBLICATIONS

International Search Report (PCT/ISA/210) dated Mar. 22, 2013, by the French Patent Office as the International Searching Authority for International Application No. PCT/FR2013/050229.
(Continued)

*Primary Examiner* — Lisa Caputo
*Assistant Examiner* — Alex Devito
(74) *Attorney, Agent, or Firm* — Buchanan Ingersoll & Rooney P.C.

(57) ABSTRACT

A method of constructing a model of permeation to mixtures of solvents of a multilayer polymer structure with n monolayers and its associated computer program. For example, selecting several initial compositions of solvent mixture E1 to Ey, carrying out a sorption measurement and a measurement of diffusion, discretizing said multilayer structure in space and time, estimating partial fluxes of each of the
(Continued)

compounds of said composition of solvent mixture between each elementary slice of said multilayer structure, estimating on the one hand a maximal sorption ceiling of said downstream monolayer B and on the other hand the composition of solvent mixture at inlet of said downstream monolayer B, performing a mass balance from slice to slice as a function of time, adjusting the profile of concentrations, storing the concentration profiles and the partial fluxes obtained.

11 Claims, 6 Drawing Sheets

(51) Int. Cl.
    *B01D 69/12* (2006.01)
    *B01D 71/26* (2006.01)
    *B01D 71/38* (2006.01)

(52) U.S. Cl.
    CPC ............. *B01D 71/38* (2013.01); *G01N 15/08* (2013.01); *G01N 2015/0866* (2013.01)

(56) References Cited

U.S. PATENT DOCUMENTS

| | | | |
|---|---|---|---|
| 6,715,511 | B2 | 4/2004 | Yamamoto et al. |
| 6,778,413 | B2 | 8/2004 | Kates |
| 2006/0008604 | A1 | 1/2006 | Flat et al. |

FOREIGN PATENT DOCUMENTS

| | | |
|---|---|---|
| CN | 1425552 A | 6/2003 |
| CN | 1721178 A | 1/2006 |
| CN | 1277336 C | 9/2006 |
| EP | 1 607 213 A1 | 12/2005 |

OTHER PUBLICATIONS

Sohir Benrabah et al., "Modeling of Fuel Permeation in Multilayer Automotive Plastic Fuel Tanks", SAE International, vol. 4, No. 1, Apr. 12, 2011, 5 pages, XP-008155348.

Mitesh R. Shah et al., Analysis of Transient Permeation As a Technique for Determinatin of Sorption and Diffusion in Supported Membranes, Journal of Membrane Science, vol. 280, No. 1-2, Sep. 1, 2006, pp. 454-460, XP-024931983.

Anne Jonquieres et al., "From Binary to Ternary Systems: General Behaviour and Modelling of Membrane Sorption in Purely Organic Systems Strongly Deviating From Ideality by Uniquac and Related Models", Journal of Membrane Science, vol. 174, No. 2, Jul. 1, 2000, pp. 255-275, XP-004201926.

Robert Clement et al., "An Original Automated Desorption Apparatus for Measuring Multi-Component Sorption Properties of Barrier Polymer Films", Journal of Membrane Science, vol. 302, No. 1-2, Aug. 24, 2007, pp. 95-101, XP-022210825.

Disclosed Anonymously, "Toughened Nylon-66 (Dupont FE4250HP) With Zero Ethanol Fuel Permeability for Flexible Fuel Vehicle Fuel System", Research Disclosure, vol. 512, No. 95, Dec. 1, 2006, p. 1657, XP-007136968.

Office Action dated Nov. 24, 2015, by the State Intellectual Property Office of the People's Republic of China in corresponding Chinese Patent Application No. 2013800187435. (1 page).

\* cited by examiner

METHOD OF MODELING PERMEATION TO ESSENCES OF A MULTILAYER POLYMER STRUCTURE

TECHNICAL FIELD

The disclosure relates to the field of the permeation of mixtures of solvents through a multilayer polymer structure. Permeation means the transport of a fluid, such as a solvent mixture, through a membrane. More precisely, it is the amount of each of the components of a solvent mixture passing through a multilayer polymer structure.

More particularly, embodiments of the disclosure relate to a method of modeling the permeation of mixtures of solvents through a multilayer polymer structure, notably essences and more particularly essences of the fuel type. Embodiments of the disclosure further relate to any container comprising a multilayer polymer structure for which permeation is modeled according to the method of modeling and in particular to fuel tanks, and finally to a computer program implementing the method of modeling.

BACKGROUND

Historically, the containers or tanks used for storage or transport of chemicals were made of metal. These metal articles have gradually been replaced with single-layer plastics, which are lighter and are easier to use, allowing tanks to be made with complex geometries, and are not susceptible to corrosion. However, these single-layer plastic tanks no longer comply with the regulations on emissions and it is therefore necessary to develop plastic solutions with better performance in terms of barrier properties than the single-layer solutions. One route used industrially today is the multilayer plastic structure combining different materials judiciously selected in order to increase the barrier properties of said structure. The transport sector notably is constantly seeking to reduce the weight of vehicles, to lower their emissions and their energy consumption. However, these lightweight materials must meet the strictest hermeticity standards. Therefore the polymer wall of a fuel tank must have good barrier properties to limit mass transfer from the fuels to the environment. The word barrier is used in the description to describe barrier materials to essences. To perform its barrier role best, the wall of the tank is notably formed from a multilayer polymer structure, each of the layers performing a role of barrier to at least one of the compounds in the fuel.

Environmental standards are more and more stringent, for maximum reduction of emissions of hydrocarbons into the environment. Thus, the European standard Euro V, in force since September 2009, limits emission to 2.0 g per test, and a test may take up to 36 hours. The American standard PZEV (acronym for "Partial Zero Emission Vehicle") limits the emissions to 0.35 g per test of 3 days for the whole vehicle. Consequently, in this context, it is necessary to optimize the walls of the fuel tanks, by optimizing their permeation to essences, for maximum limitation of any loss of fuel to the environment.

An essence is a mixture of aromatic and aliphatic compounds and of an oxygen-containing compound, very often alcohol. Now, polymers are not barriers to all the compounds contained in an essence and not all polymers are barriers to the same compounds contained in an essence. Thus, polyethylene for example is a barrier to alcohol, but not to toluene, which is an aromatic compound that is a constituent of the essence.

The key materials used in the barrier structures are characterized by low levels of swelling when they are brought into contact with the essences, and by reduced mobility of the small molecules diffusing in the polymer matrix. This imposes very long delays for equilibration for the industrial structures of multilayer tanks, typically of the order of a year. Moreover, experimental investigation of these phenomena requires accumulating numerous measurements. These considerations have led the applicant to perform these characterizations on the basis of much thinner films than those that are used in the walls of tanks. In fact, each time the thickness of a film is halved, its time for semi sorption/desorption is approximately divided by four and the mass flow is amplified by a factor of two. The experimental measurements are still very time-consuming since they take on average from 1 to 3 months for essence lines with a thickness of 1 mm, and at least a year for tanks with a minimum thickness of 3 mm.

In view of the extremely long time for obtaining measurements allowing validation, or otherwise, of multilayer polymer structures for making a tank wall, it became apparent that it is necessary to develop models to allow preselection of structures that are usable and comply with the standards. With such modeling it is possible to validate structures in one day, whereas the experiments take several months.

There are models for predicting permeability through multilayer structures, but these models are used in the context of investigation of permeability to simple gases, such as carbon dioxide $CO_2$, oxygen $O_2$, or nitrogen $N_2$, or to water vapor. These models make it possible for example to predict the storage life of foodstuffs by estimating the oxygen permeability of a multilayer membrane surrounding the foodstuffs. However, these models do not allow prediction of the permeability of multilayer structures to an essence. In fact, an essence is a solvent mixture and the composition of the essence varies over the thickness of the multilayer structure as a function of the nature and thickness of the layer traversed. Various parameters must therefore be taken into account, for example interactions of the essence/polymer type (sorption), the resistance at the interface between two polymer layers and diffusion of the essence, and of each of its constituents, in each layer.

On the basis of laws of diffusion (Fick's Law for example) and laws of sorption (UNIQUAC model for example), defined for each monolayer, the behavior of multilayer structures combining different materials is predicted, and thus structures of tanks are validated, or otherwise, with respect to ever more stringent environmental standards.

A method is also known from the document with the title "Modeling of fuel permeation in multilayer automotive plastic fuel tanks", published in April 2011 by Benrabah, Thibault and DiRaddo, for modeling the permeation of essences through multilayer materials, such as tanks, but the hypotheses adopted in this method are very limiting, do not apply to all of the layers of the tanks described and consequently do not allow a reliable result to be obtained.

SUMMARY

Embodiments of the disclosure therefore aim to remedy at least one of the drawbacks of the known art. An embodiment of the disclosure notably aims to provide modeling of the behavior of an essence in a multilayer polymer structure so that a tank structure can be validated, or otherwise, simply, quickly and efficiently.

For this purpose, the disclosure relates to a method for modeling the permeation of mixtures of solvents through a multilayer polymer structure with n monolayers (n≥2), said method being characterized mainly in that it comprises carrying out the following steps:

1) selecting several initial compositions of solvent mixture E1 to Ey, each composition of solvent mixture comprising a mixture of at least two compounds selected from an oxygen-containing compound (a), an aliphatic compound (b) and an aromatic compound (c), in various proportions,
2) for each composition of solvent mixture E1 to Ey, carry out the following steps:
   a. for each monolayer included in the constitution of the multilayer structure, carry out:
      measurement of sorption, consisting of measuring an amount of each compound of said composition of solvent mixture, absorbed by said monolayer; this step thus makes it possible to obtain, based on these measurement data, a model that corresponds to the thermodynamic law of sorption for each monolayer,
      measurement of diffusion, by measuring partial fluxes of each compound of said composition of solvent mixture through said monolayer; this step thus makes it possible to obtain, based on these measurement data, a model that corresponds to the kinetic law of diffusion for each monolayer,
   b. discretize said multilayer structure in space and time, the discretization in space consisting of cutting up, virtually, each monolayer of the multilayer structure into X elementary slices, and then regarding said multilayer structure with n monolayers as a succession of (n−1) bilayers, each bilayer comprising an upstream monolayer A and a downstream monolayer B,
   c. based on the data measured for each monolayer in step 2.a:
      c.1. estimate partial fluxes of each of the compounds of said composition of solvent mixture between each elementary slice of said multilayer structure,
      c.2. at the interface between each upstream monolayer A and downstream monolayer B of said multilayer structure, estimate on the one hand a maximal sorption ceiling of said downstream monolayer B and on the other hand the composition of solvent mixture at inlet of said downstream monolayer B, said composition being limited to said estimated maximal sorption ceiling,
      c.3. perform a mass balance from slice to slice as a function of time, so as to obtain a concentration profile of each compound of said composition of solvent mixture in said multilayer structure as a function of time,
      c.4. adjust the profile of concentrations, the profile of partial fluxes and the thicknesses of the elementary slices, taking into account monodirectional swelling of the structure,
      c.5. repeat steps c1 to c4 until the partial fluxes are conservative at every point of the structure,
   d. once the partial fluxes are conservative, store the concentration profiles and the partial fluxes obtained According to another characteristic feature, the solvent mixture is an essence comprising a mixture of at least two compounds selected from an oxygen-containing compound (a), an aliphatic compound (b) and an aromatic compound (c), in various proportions. More particularly, the essence comprises a mixture of at least one oxygen-containing compound (a), an aliphatic compound (b) and an aromatic compound (c), in various proportions.

Modeling the permeation of the essences through a multilayer structure thus makes it possible to predict all the partial fluxes of the various solvents (ethanol, iso-octane and toluene) through multilayer structures that are made up of several layers of polymers of different natures and thicknesses. The method of modeling therefore makes it possible to optimize tank structures based on calculations and allows a saving of time, and therefore of money, when designing the tanks. The method also makes it possible to optimize on the one hand the thickness of the different layers of the structure and on the other hand the order of stacking of the materials constituting the different layers of the multilayer structure.

According to other optional features of the method:
   prior to step 2c.1. for estimating the partial fluxes, an initialization step consists of calculating, from the values of sorption at inlet and outlet of the multilayer structure, corresponding activities of each of the compounds of said composition of solvent mixture at inlet and outlet of said structure, and then creating a linear activity profile for each of the solvents from inlet to outlet of the structure and then, based on this activity profile, estimating local concentrations of each of the compounds of said composition of solvent mixture in each slice of said multilayer structure, as well as the thickness of the elementary slices, taking into account monodirectional swelling of said multilayer structure,
   step 2c.1. of estimating the partial fluxes consists of estimating on the one hand diffusion fluxes, from the local concentrations of each of the compounds of said composition of solvent mixture in each elementary slice, and on the other hand convection fluxes, from the partial fluxes measured in step 2a and the local concentrations of each of the compounds of said composition of solvent mixture in each elementary slice,
   the treatment at the interface between two monolayers of polymer materials different from step 2c.2 is based on the fact that there is equality of the flows between two adjacent monolayers and that the concentration of each of the compounds at inlet of the downstream monolayer B cannot exceed the sorption ceiling,
   the sorption ceiling is calculated from the activities of each of the compounds of said composition of solvent mixture, on the assumption that there is continuity of activity between the last slice of an upstream monolayer A overlapping with a first slice of a downstream monolayer B,
   each essence composition E1 to Ey comprises a proportion by volume (%) of one of the compounds (a) that varies from one composition to another, whereas the other compounds (b, c) have an identical proportion by volume,
   each essence composition comprises a mixture of several compounds (a, b, c) selected from ethanol (a), iso-octane (b), and toluene (c).

An embodiment of the disclosure further relates to a container made in a multilayer polymer structure for which the permeation of mixtures of solvents is modeled by the method of modeling described above. An embodiment of the disclosure relates in particular to fuel tanks.

Finally, an embodiment of the disclosure also relates to a computer program comprising program code instructions for executing the steps of the method of modeling described above, when said program is executed by a processor.

BRIEF DESCRIPTION OF THE DRAWINGS

Other particular features and advantages of the disclosure will become clear on reading the description that is given below as an illustrative, nonlimiting example, in conjunction with the figures, showing.

DETAILED DESCRIPTION

In the rest of the description, the term essence denotes a solvent mixture comprising at least two compounds selected from an oxygen-containing compound (a), an aliphatic compound (b) and an aromatic compound (c), in various proportions. As an example, this may be a perfume or a fuel.

In the example described below it is a fuel composed of aromatic hydrocarbons, aliphatic hydrocarbons and an oxygen-containing compound. In the present case, a so-called model essence is used. It is composed of toluene (of formula $C_7H_8$, representing the aromatics), isooctane (of formula $C_8H_{18}$, representing the aliphatics) and ethanol (of formula $C_2H_6O$, representing the oxygen-containing compound). However, the disclosure is not limited to these compounds.

Figure 1:
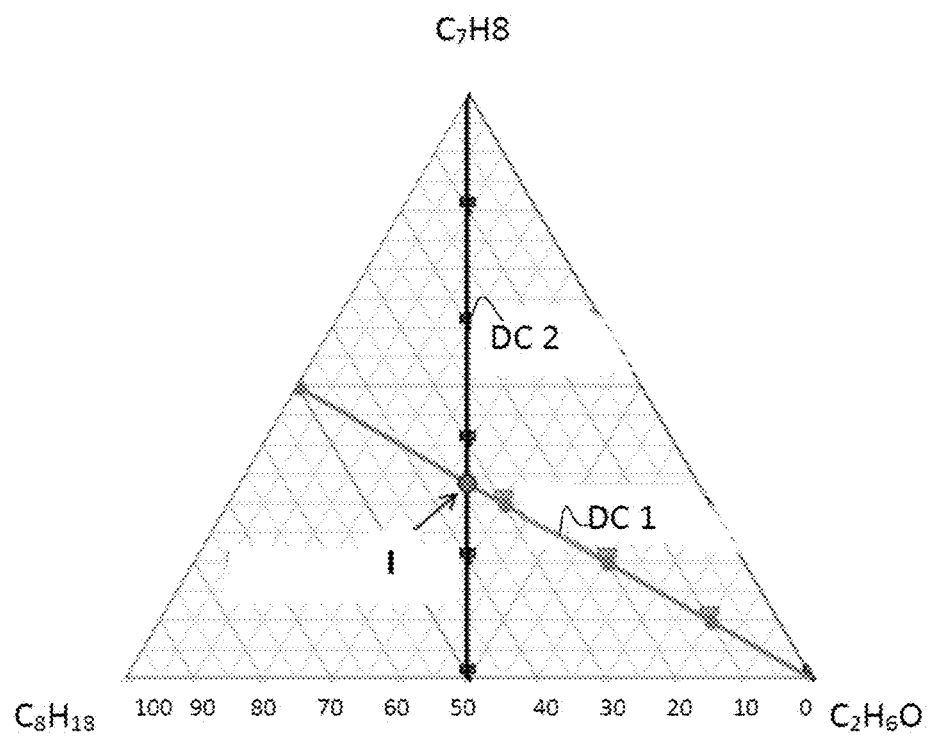
FIG. 1, a schematic representation of a ternary diagram corresponding to mixtures of solvents used in compositions of model essences, FIG. 2, a schematic diagram of a "sorption-diffusion" model forming the basis of the permeability of a single-layer polymer structure, FIG. 3, a basic diagram of a method of modeling according to the disclosure, FIG. 4, a basic diagram of a multilayer structure cut up virtually into elementary slices to allow a fine numerical calculation used in the method of modeling according to an embodiment of the disclosure, FIG. 5, curves representing the partial fluxes, measured and calculated, of the various compounds of an essence with different compositions in a given two-layer structure, FIG. 6, curves representing the partial fluxes, measured and calculated, of the various compounds of an essence with different compositions in another two-layer structure, FIG. 7, curves representing the partial fluxes, measured and calculated, of the various compounds of an essence with different compositions in another three-layer structure, FIG. 8, curves representing the calculated partial fluxes of the different compounds of an essence as a function of the thickness of the layer arranged in the middle of a three-layer structure, FIG. 9, curves representing the calculated partial fluxes of the different compounds of an essence as a function of the thickness of the last layer of the same three-layer structure as FIG. 8, FIG. 10, curves representing the calculated partial fluxes of the different compounds of an essence as a function of the thickness of the first layer of the same three-layer structure as FIG. 8, FIG. 11, curves representing the calculated partial fluxes of the different compounds of an essence as a function of the proportion by volume of oxygen-containing compound in the composition of essence, in a five-layer structure.

FIG. 1 shows a ternary diagram corresponding to different mixtures of these three compounds used in different compositions of model essences. This diagram shows two specific straight lines called ethanol tie line, referenced DC1, and toluene tie line, referenced DC2. The ethanol tie line, DC1, corresponds to a composition with equal volumes of toluene and iso-octane in which the percentage by volume of ethanol varies from 0 to 100%. This tie line allows evaluation of the effect of adding oxygenated compounds on the fuel tanks. Moreover, the toluene tie line, DC2, corresponds to a composition with equal volumes of ethanol and iso-octane, in which the percentage by volume of toluene varies between 0 and 100%. These two tie lines have a point of intersection I which makes it possible to verify the consistency of the experimental values obtained for these two lines.

For the purposes of modeling, several different compositions of essence E1 to Ey are selected, for example between 5 and 10 different compositions, preferably between 6 and 8, along at least one of the two tie lines, for example along the ethanol tie line DC1.

Figure 2:
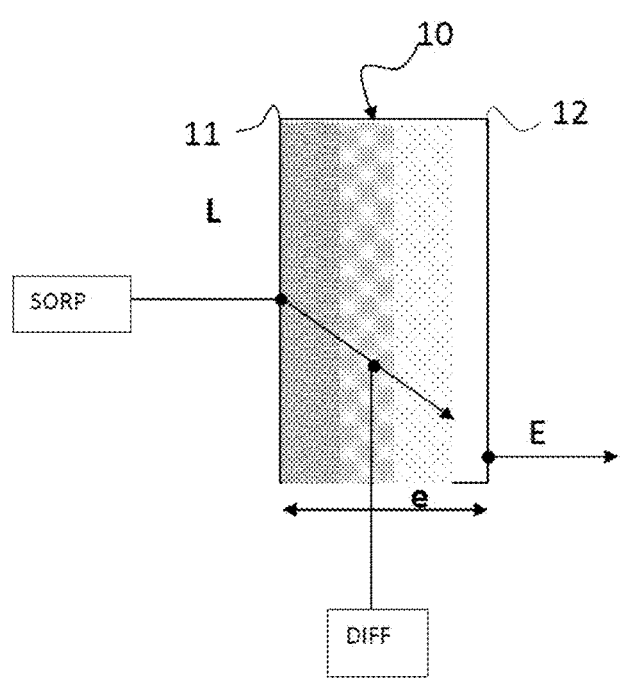

The permeability of a single-layer polymer membrane 10 is based essentially on the "sorption-diffusion" model, as illustrated in FIG. 2. A first measurement consists of measuring the sorption SORP on the upstream face 11 of the membrane 10, i.e. the face in direct contact with the liquid mixture L. The membrane 10 swells selectively opposite the adjacent liquid mixture L. The selectivity is due to the affinity of the material forming the membrane for the different compounds present in the liquid mixture L. This means that the composition of the liquid that enters the upstream face 11 of the membrane 10 is generally very different from that of the liquid mixture L. A second measurement consists of measuring the diffusion DIFF, i.e. the amount of matter that diffuses from the upstream face 11 to the downstream face 12 of the membrane 10. The diffusion DIFF arises from the kinetics. It depends on the concentration gradient of each compound of the liquid mixture L, migrating from the upstream face 11 to the downstream face 12. Finally, another phenomenon, which is not taken into account for calculating the permeability, concerns the desorption E of the compounds absorbed, by evaporation on the downstream face 12. The molecules of compounds that have migrated to the downstream face 12 are desorbed by evaporation E. This desorption has no effect on the calculation of the permeation of the membrane as this step is not limiting in the permeation process in the conditions considered.

By convention, for all the multilayer structures, the first material named is the one in contact with the liquid mixture. For example, in the case of a two-layer structure called "Binder/EVOH", the layer of binder is located upstream, in contact with the liquid mixture, and EVOH is downstream.

Figure 3:
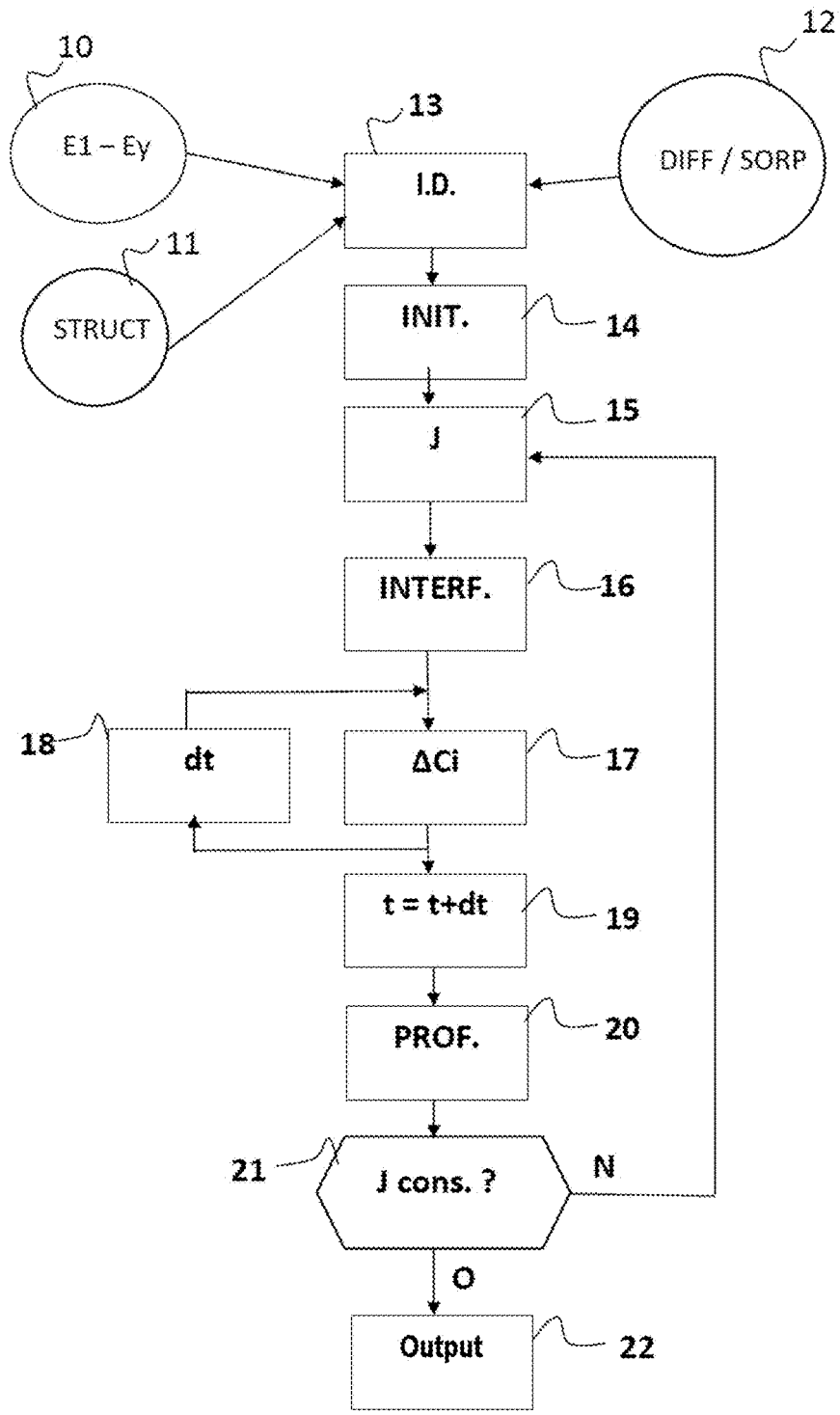

FIG. 3 shows a basic diagram of the method of modeling according to an embodiment of the disclosure.

Steps 10, 11, 12, and 13: Input Data and Initialization of the Calculation

In order to be able to model the permeability of a multilayer structure to an essence, it is necessary to know the sorption and diffusion behavior of each of the compounds of the essence in each polymer constituting the multilayer structure. That is why the modeling is based on experimental measurements of sorption and diffusion taken at 50° C. on each of the monolayers making up the multilayer structure, for the whole range of compositions of the ethanol/iso-octane/toluene ternary system.

For this purpose, for each of the compositions of model essence E1 to Ey selected (step 10), preliminary experimental measurements of sorption and diffusion are performed on polymer monolayers, with thickness between 25 and 200 µm, included in the constitution of the multilayer structure (STRUCT 11) for which the calculation of permeability to the essences is to be performed. Thus, these measurements enable us to know the behavior of each of the solvents of the essence in each of the polymer materials of the multilayer structure, taken separately.

The swelling of a single-layer polymer by solvents may be regarded as a thermodynamic equilibrium between two different phases. The dry polymer, which is in contact with the solvents, creates a chemical potential gradient. This difference of chemical potential plays the role of motive force to provide mass transfer and penetration of the molecules of solvents into the polymer material. Following the transient regime, a stationary state is established with the presence of a constant amount of solvent in the polymer. From the standpoint of thermodynamics, this equilibrium is reflected in equality of the chemical potentials of the different solvents in the liquid phase, i.e. in the model essence, and in the solid phase, i.e. the swollen polymer.

Measurement of sorption then consists of determining the overall swelling and the partial swellings of the polymer in a liquid at thermodynamic equilibrium, which corresponds to obtaining a constant mass for the swollen polymer. This sorption measurement is performed for each of the solvents of each of the compositions of essence selected E1 to Ey in step 10. For this, the polymer constituting a monolayer is immersed in each essence composition E1 to Ey and measurements of weight of swollen polymer are carried out until the weight is constant, which may take several months. Then the partial swellings are measured relating to each constituent of the essence after desorption of the solvents for each essence composition, with quantification by gas chromatography.

In its turn, diffusion is an irreversible transport phenomenon that is reflected in migration of chemical species in a medium from the regions of higher chemical potential to those of lower chemical potential. This phenomenon is for example described by Fick's first law, which states that the diffusion flux is proportional to the concentration gradient. Measurement of diffusion consists of measuring, in steady-state conditions, the partial fluxes of each solvent for each model essence composition E1 to Ey migrating over time through a polymer monolayer, i.e. the amount of a compound passing through the monolayer in unit time and unit area. This measurement is advantageously performed by means of a permeameter coupled to a gas chromatograph for on-line analysis of the permeate.

The experimental measurements thus performed then constitute the input data I.D. (step 13) for the method of modeling the permeation of a multilayer structure.

Moreover, for carrying out the method of modeling, it is further necessary to know the laws of sorption SORP (step 12) that relate the activities of the three solvents to the concentrations measured at sorption equilibrium for each polymer material. To be able to model the sorption equilibria, it is necessary to know the activities of the different solvents in the model mixtures of fuels used. The activities of ethanol, iso-octane and toluene of each model essence composition are calculated at 50° C., the temperature selected for the measurements of sorption. This calculation is performed on the basis of the model known as UNIQUAC (UNIversal QUAsi Chemical theory) applied to the corresponding ternary liquid mixtures. Sorption measurements are carried out to determine the composition of the swollen polymer at 50° C., for different compositions of model essences corresponding to at least one of the two ethanol or toluene tie lines. The activities of the different solvents in the swollen polymer are then calculated from sorption measurements carried out for determining the composition of a swollen polymer at 50° C. These calculations are carried out using the UNIQUAC model applied to the quaternary systems (ethanol/iso-octane/toluene/swollen polymer). The parameters of polymer/solvent binary interaction of the UNIQUAC model are finally adjusted so that the results of the modeling and the results of the measurements converge, thus obtaining a thermodynamic law of optimized sorption (12) for each monolayer. Generalization of the model is then possible and the activities of the three solvents in a swollen polymer can be calculated when the composition of the swollen polymer is known.

Finally, for carrying out the method of modeling, it is also necessary to know the laws of diffusion DIFF (step 12) to take account of the variation of the coefficients of diffusion of these solvents as a function of their local concentration in each polymer material considered. By measuring the partial fluxes of each compound of the composition of essence through each monolayer, it is possible to obtain, for each monolayer, a model that gives a kinetic law of diffusion for each compound.

Based on measurement of the sorption equilibria for the different polymers, the concentrations of the three solvents upstream of the structure, i.e. at inlet of the first monolayer of the multilayer structure, are known and fixed by the experimental data. The concentrations downstream, i.e. at outlet of the last monolayer of the multilayer structure, are always considered to be equal to zero. The boundary conditions are thus defined upstream and downstream from the multilayer structure for numerical calculation of the partial fluxes.

Finally, starting from the principle that a multilayer structure with n monolayers may be formally regarded as a succession of (n–1) bilayers, each bilayer comprising an upstream monolayer A and a downstream monolayer B, the predictive calculations for a multilayer structure are performed according to a repetition of calculations on the various bilayers involved.

Steps 14 to 21: Treatment for Each Composition E1 to Ey (which May be Carried Out Indiscriminately in Parallel or in Series)

Figure 4:
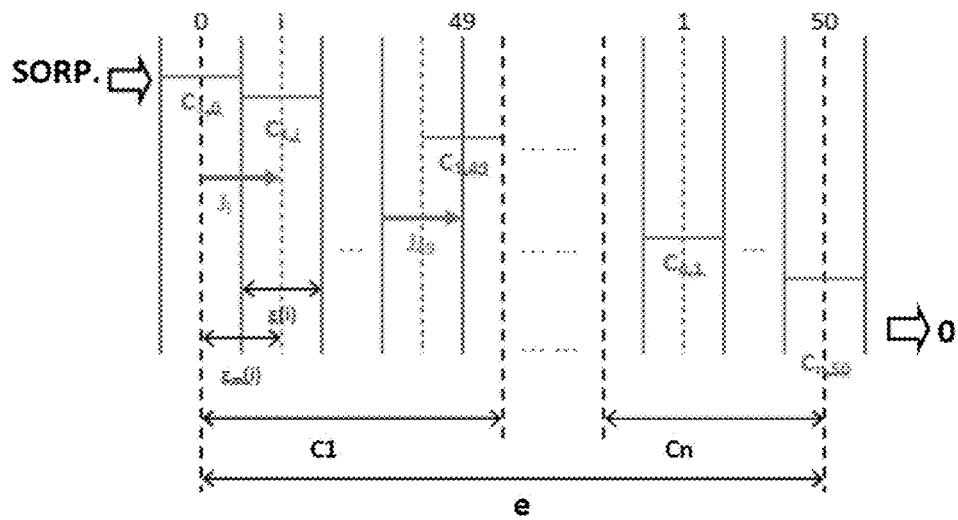

After collecting all the input data I.D. to be taken into account for the modeling, the next step 14 of the method of modeling consists of initializing the concentration profiles in the multilayer structure. For this, the multilayer structure is discretized in space and time. The discretization of the multilayer structure in space is represented schematically in FIG. 4. The multilayer structure, of thickness e, is cut up virtually into elementary slices that are sufficiently numerous for proper account to be taken of the variations of the quantities in each slice. This cutting-up is carried out depending on the thickness e of the structure, which corresponds to the direction of transfer of the three solvents. The number X of elementary slices is for example between 45 and 55 for each polymer monolayer. For example it is fixed at 50 for each polymer monolayer. Each monolayer c1, . . . $c_n$, making up the multilayer structure has its own characteristic thickness, e1 . . . $e_n$ respectively. The number of monolayers constituting the multilayer structure is for example limited to 7. However, this number may naturally be higher depending on the nature of the multilayer structure to be investigated.

The interfaces of each monolayer are centered in the first and last elementary slices for taking into account the inlet and outlet of each monolayer. At each interface between two adjacent polymer monolayers, the last elementary slice of the upstream layer A and the first elementary slice of the downstream layer B are overlapping. To ensure continuity of the flows, the entering and leaving flows that correspond to these two overlapping slices are kept equal. The real thickness e of the multilayer structure is comprised between the center of the first elementary slice and the center of the last elementary slice of the structure. Once the inlet and outlet compositions are known, the corresponding activities are also calculated using a known model, such as the UNIQUAC model for example. Next, linear activity profiles are created for each of the solvents considered from inlet to outlet, continuously through all the monolayers making up the multilayer structure. The local concentrations Ci of each solvent of the model essence composition are then calculated for each slice, from the activity profiles thus created.

Taking into account the local concentrations, the thicknesses $\varepsilon(i)$ of each elementary slice are recalculated according to a monodirectional expansion rule. The swelling of the structure is considered to be monodirectional. It takes place in the same direction as the migration of the species of solvent of the model essence. The expansion of the thickness of the slices, induced by the swelling of the polymer, is calculated with the aid of a coefficient of expansion Expan (i), which depends on the volume dVi of solvent absorbed in the polymer, and the volume V0 of the dry polymer. The thickness of an elementary slice $\varepsilon(i)$, taking the swelling into account, becomes: $\varepsilon(i)=\varepsilon 0(i)\times Expan(i)$, where $\varepsilon 0(i)$ represents the thickness of a slice i of the dry polymer. The phenomenon of swelling tends to reduce the concentration gradients owing to the increase in the thickness of the membrane. After calculating the thickness of an elementary slice $\varepsilon(i)$ of swollen polymer, it is then possible to estimate the concentration gradient of each solvent in consequence in each elementary slice.

Concerning discretization in time, a time increment dt makes it possible to calculate a mass balance in each elementary slice of the structure. This mass balance then allows the concentration profiles of each of the solvents in the multilayer structure to be estimated.

Starting from the local concentrations of each of the solvents, calculated in step 14, the next step 15 of the method of modeling consists of calculating the partial fluxes. Thus, to calculate the diffusion partial fluxes, we apply Fick's first law, according to which the diffusion flux is proportional to the concentration gradient. Fick's first law is applied for each so-called "mixed" slice, i.e. for each slice made up of two adjacent half-slices, of thickness referenced $\varepsilon m(i)$ in FIG. 4, to calculate the diffusion partial fluxes through each slice interface. The calculation uses the values of local concentrations and of thickness of each slice previously calculated in step 14.

Advantageously, in addition the convection partial fluxes are taken into account. Knowing that the overall partial flux measured is equal to the sum of the diffusion partial fluxes and the convection partial fluxes, the convection partial fluxes are deduced from the calculated local concentrations and the measured overall partial flux. In this case, an iterative calculation is performed to take account of the convection fluxes. This calculation is continued until the change in the partial fluxes becomes negligible.

The next step 16 consists of carrying out a treatment at the interface between each polymer monolayer included in the constitution of the multilayer polymer structure. According to the various configurations of the multilayer film, it is generally possible to distinguish two kinds of limitations to transfer at the interface. To illustrate these two kinds of limitation to transfer, the example of a two-layer film, comprising an upstream monolayer A and a downstream monolayer B, is described below.

The first limitation relates to the case when the downstream monolayer B is more permeable to a species than the upstream monolayer A. In this case, the concentration profile of this species in the upstream monolayer A will become sloping to respond to the depletion created by the downstream monolayer B. Removal is then quicker than supply, and therefore no accumulation of species occurs at the interface. The concentration of this species in the downstream monolayer B will therefore be low. Consequently, the activity profile is also discontinuous, as no equilibrium is established at the interface, and transfer is controlled solely by the upstream diffusion laws, which corresponds to a kinetic limitation.

The second limitation relates to the case when, in a symmetrical manner, the downstream monolayer B has a greater barrier effect than the upstream monolayer A for a given species. In this case, the concentration profile of this species in the upstream monolayer A will level off to allow equality of the flows on either side of the interface. With the concentration gradient decreasing, accumulation of matter then takes place in the upstream monolayer A. This accumulation of matter is, however, limited by the sorption thermodynamics, which fixes the upper limit of the concentrations of each solvent for each polymer for the activities considered. This theoretical upper limit may be calculated assuming thermodynamic equilibrium at the interface. This equilibrium is reflected in equality of the activity for all of the species on either side of the interface. In this case, the profiles of the activities are therefore continuous on the whole bilayer. In contrast to the preceding case, the limiting factor is then the sorption ceiling, which is fixed by the thermodynamic properties. This particular case therefore corresponds to a thermodynamic limitation.

The concentration profiles through a multilayer structure are discontinuous at the level of the interfaces between the different monolayers. The profile differs depending on the properties of each polymer and of each solvent considered. For calculating such a concentration profile, it is assumed that there is continuity of the activity of each species in steady-state conditions in the case of equilibrium at the interface. Then the sorption ceilings for each downstream monolayer B are estimated assuming thermodynamic equilibrium between the two adjacent slices. For calculating the activities of each solvent in the polymer at the downstream interface of the upstream monolayer A, it is therefore necessary to make use of a known sorption model, such as the UNIQUAC model for example. Once these activities are known, and assuming continuity thereof in the case of equilibrium at the interface, it becomes possible, by means of a reverse calculation, to calculate the composition of the essence entering upstream of the next downstream monolayer B.

Evaluation of the composition of the model essence E1 to Ey considered is therefore performed at the inlet of each monolayer. If this composition exceeds the thermodynamic ceiling calculated initially, it is then limited to the value of this ceiling.

In step 17, a mass balance is then performed by applying Fick's second law, which concerns the variation of the concentration in time and space. This calculation step allows evolution of the local concentration of each solvent of the composition of essence considered in each elementary slice, and therefore the concentration profile in the multilayer structure, as a function of time. The concentration profiles and the partial fluxes are modified at each time increment dt, applying mass balances from slice to slice on the whole multilayer structure.

The change in concentration is calculated from a time increment dt and from the balance of the partial fluxes. It must be limited by selecting a suitable time increment for ensuring convergence of the calculation, notably when the monolayers have very different permeabilities. In fact, the most permeable material contributes considerably to limiting the rate of change of the concentration profiles in the least permeable materials by setting low values for the time increment dt. This is reflected in an increase, which may be very substantial, in the calculation time required to reach a steady state.

Step 18: The time increment dt is adjusted automatically so that the largest relative concentration change dC/C in each monolayer does not exceed an identical value in the whole structure. If the relative concentration change dC/C exceeds this limit, the time increment dt is increased (new dt=old dt*1.01), otherwise it is decreased by a factor of 0.8 for example. This manner of discretizing the multilayer structure in time generally makes it possible to avoid problems of divergence of the calculation. Accordingly, the mass balances in each layer remain consistent, i.e. the outlet flow is equal to the inlet flow, while accelerating establishment of the profiles in the least permeable materials.

Step 19: After adjustment of the time increment dt and establishment of the variation of the local concentrations, the time is incremented by dt.

Step 20: The concentration profiles PROF of each compound of the model essence in the multilayer structure are updated, and the corresponding thicknesses of the elementary slices are adjusted taking into account the monodirectional swelling of the multilayer structure.

Step 21: A test is performed to check whether the calculated partial fluxes are conservative throughout the structure, i.e. whether the changes in flux are very slight at every point of the structure. In fact, the change in flux must be less than $1/1000$ of the overall flux. Once the fluxes are identical at every point of the structure, the calculations stop, otherwise the calculation loops back to the first step of estimation of the diffusion fluxes and convection fluxes (step 15). Moreover, the calculation is adapted depending on the error obtained for the criterion of conservation of fluxes. When the system reaches steady state, the concentration profiles and the partial fluxes are stored.

Step 22: Output from the Calculation

Of course, the same calculation is carried out for the experimental data (sorption+partial fluxes) corresponding to each composition E1 to Ey of model essence.

Once the calculation has been carried out for all the experimental data, an error function is calculated by comparing the calculated and experimental fluxes. When there is no longer any improvement in the error function, the calculation stops and the optimized parameters are saved as well as the concentration profiles, the partial fluxes and the various characteristics of the system investigated.

The modeling thus performed makes it possible to optimize a multilayer polymer structure for tanks based on the calculations. It makes it possible to save a lot of time, and therefore money, in designing the tanks. Typically, a calculation takes 1 day whereas the measurements take more than a year for tanks for industrial fuels. Moreover, this modeling makes it possible to define an order of stacking of the different materials and to adjust their thicknesses. Finally, based on modeling, it is possible to consider novel materials and design novel structures not envisaged hitherto.

Example 1

Figure 5:
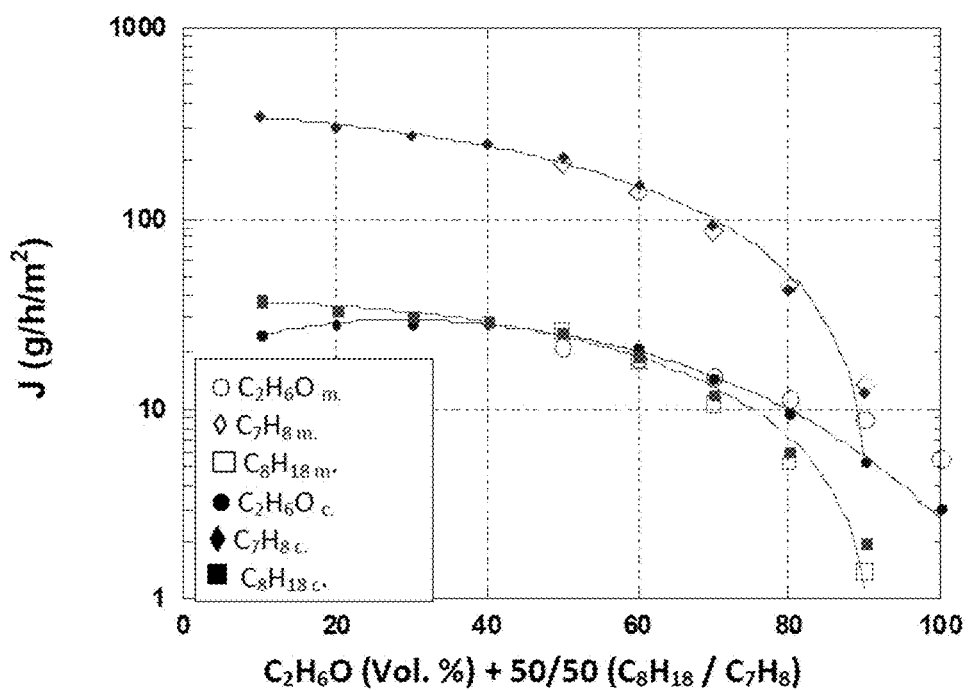

Modeling of mass transfer was performed for a two-layer structure and the results from the modeling were compared with the values measured experimentally on this same two-layer structure. The results of these comparisons are represented by the curves in FIG. 5.

The two-layer structure is a film comprising a layer of binder 9 μm thick and a layer of HDPE (high-density polyethylene) 24 μm thick. The essence is on the upstream layer side, i.e. the layer of binder. The binder used is maleic anhydride-grafted LLDPE, in other words it is linear low-density polyethylene grafted with maleic anhydride. The measurements and the modeling were carried out for different compositions of essence. Typically, the proportion by volume (%) of ethanol was varied from 0 to 100%, while keeping an identical proportion by volume between the other two hydrocarbons, iso-octane and toluene. Thus, when a composition of essence comprises 10% of ethanol, it comprises 45% of iso-octane and 45% of toluene. Similarly, when another composition of essence comprises 60% of ethanol, it comprises 20% of iso-octane and 20% of toluene. The partial fluxes of the different compounds of the essence were measured and modeled for a temperature of 50° C. The empty symbols correspond to the measurements, whereas the curves with the filled symbols correspond to the calculations.

There is very good agreement between the calculation and the measurements over the whole range of composition of the essence.

Example No. 2

Figure 6:
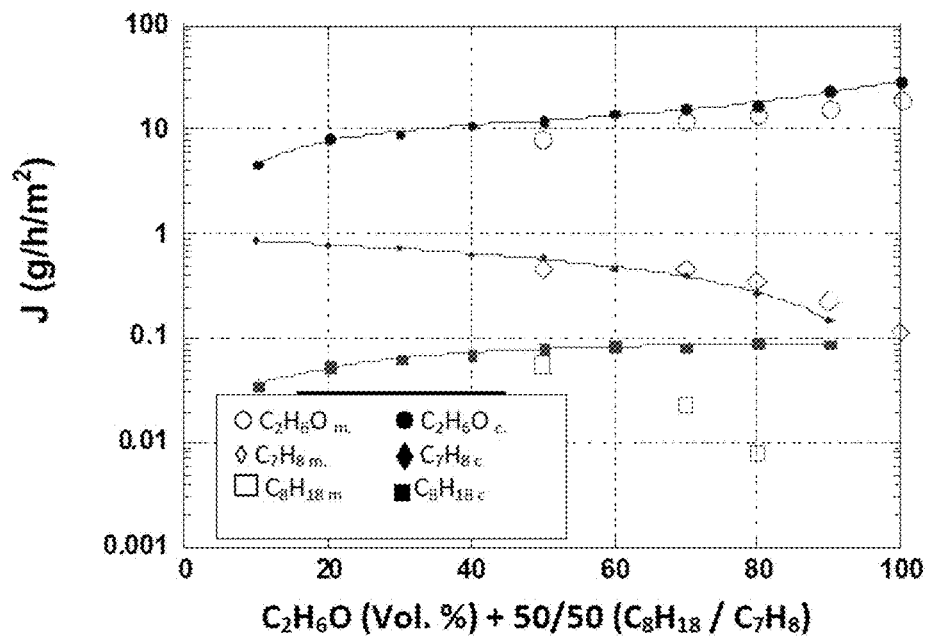

The same modeling was carried out for another two-layer film comprising an upstream layer, in contact with the essence, of EVOH (poly(ethylene-co-vinyl alcohol)) 25 μm thick and a downstream layer of binder 10 μm thick. Just as in the preceding example, the binder used is maleic anhydride-grafted LLDPE. The results of these comparisons are represented by the curves in FIG. 6.

Again in this case, there is very good agreement between the calculation (filled symbols) and the measurements (empty symbols) over the whole range of composition of the essence.

Example No. 3

Figure 7:
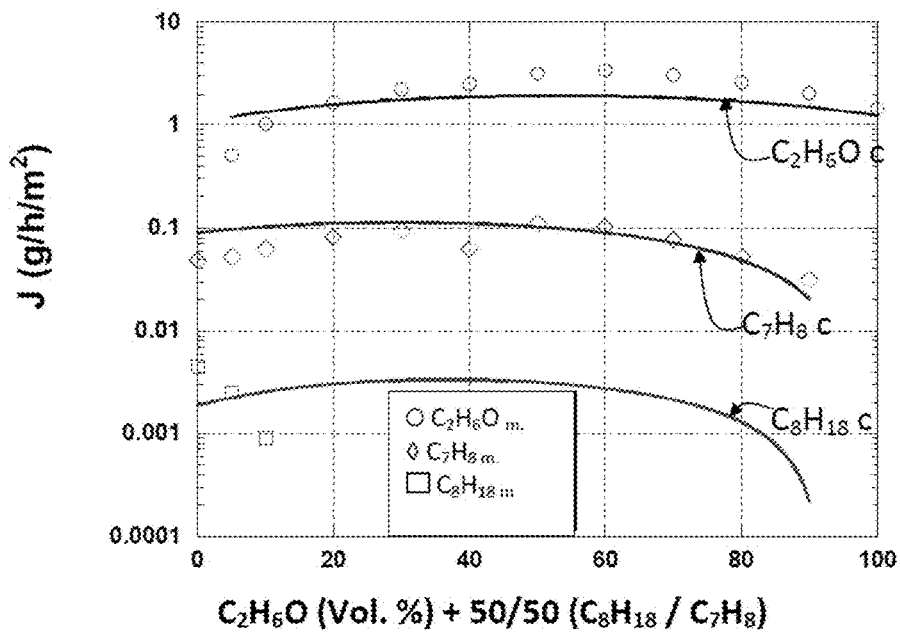

The same modeling was carried out for another three-layer film comprising an upstream layer, in contact with the essence, of HDPE (high-density polyethylene) 25 μm thick, a layer of binder (maleic anhydride-grafted LLDPE) 11 μm thick and a layer of EVOH (poly(ethylene-co-vinyl alcohol)) 10 μm thick. The results of these comparisons are represented by the curves in FIG. 7.

Once again, there is very good agreement between the calculation (curves) and the measurements (empty symbols) over the whole range of composition of the essence.

Example No. 4: Influence of the Thickness of the Layers

The influence of the thickness of each of the monolayers included in the constitution of a multilayer structure on the overall permeability of this structure was modeled.

The calculations were carried out for a structure consisting of 5 layers, varying the thickness of each of the layers independently. More precisely, the multilayer structure comprises the following layers: HDPE (high-density polyethylene)/binder (maleic anhydride-grafted LLDPE/EVOH (poly (ethylene-co-vinyl alcohol))/binder/HDPE. Moreover, the calculations are carried out at 50° C., with a model of essence E20, comprising 20% ethanol, 40% iso-octane and 40% toluene by volume.

Figure 8:
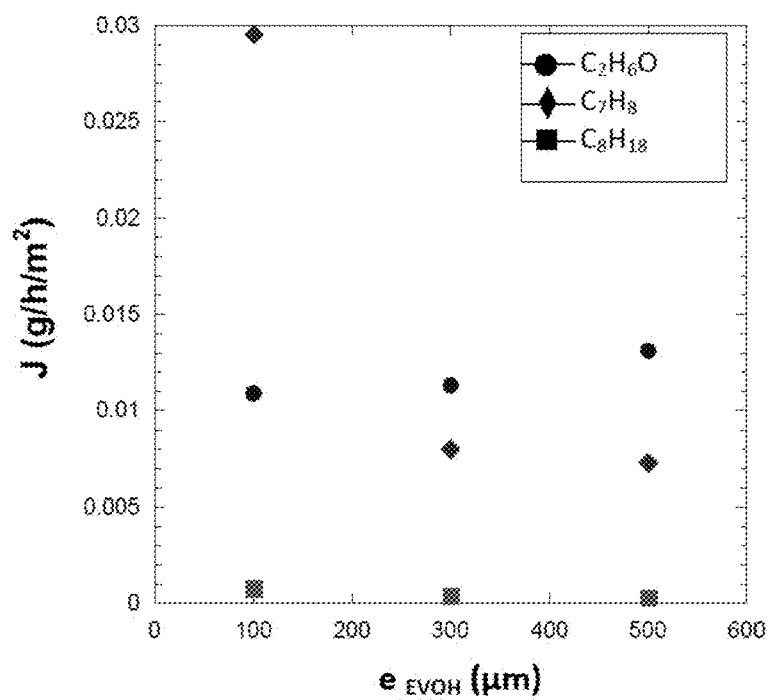

FIG. 8 shows the evolution of the partial fluxes of the different solvents of essence E20 as a function of the thickness of the layer of EVOH. It can be seen that the toluene flows decrease rapidly when the thickness of this polymer, placed in the middle of the structure, increases. The flow of iso-octane is less affected as it is already extremely low. However, it is interesting to note that the ethanol flow seems on the contrary to increase with the thickness of EVOH in the multilayer structure. To summarize, increasing the thickness of the layer of EVOH makes it possible to reduce the flows of hydrocarbons considerably, to the detriment of the overall barrier effect with respect to ethanol.

Figure 9:
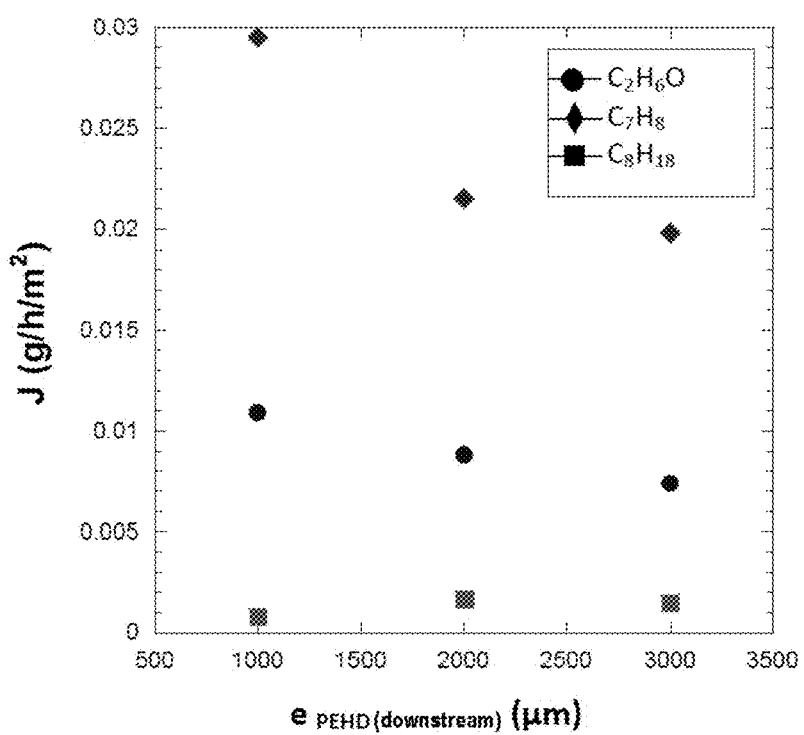
Figure 10:
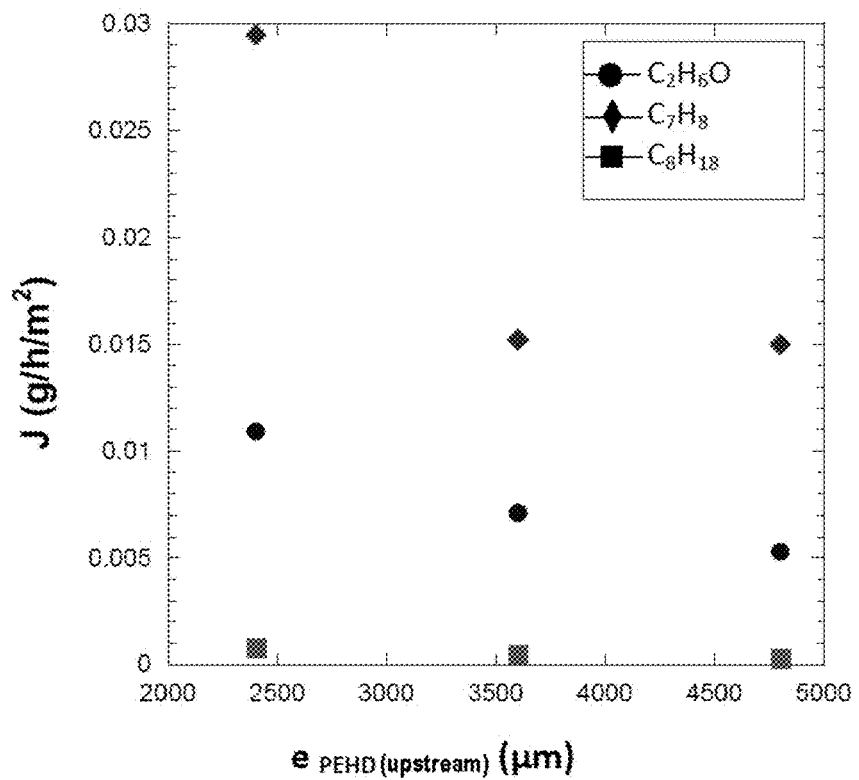

FIGS. 9 and 10 present the influence of the thickness of the layers of HDPE respectively downstream and upstream of the structure. Overall, increasing the thickness of one or other of these layers of HDPE makes it possible to decrease the partial fluxes of ethanol and toluene, whereas the effect is less clear on the flows of iso-octane, which are already extremely low for the multilayer structure considered. The effect of reduction of permeabilities is greater if the thickness of the upstream layer of HDPE increases compared to that of the downstream layer. In fact, the upstream layer of HDPE is in direct contact with the model mixture of fuels, it performs a protective role for the subsequent layers, notably EVOH. As for the downstream layer of HDPE, it has a minor role as it follows two layers of polymers with highly antagonistic effects.

Example No. 5: Influence of the Model Essence Composition

Investigation of the influence of the composition of the model essence on the permeabilities of the multilayer structures is very important for practical reasons. In fact, at present, the compositions of the essences vary considerably on an international scale depending on the producers and the legislation. The proportion of additives derived from biological routes, such as bio-ethanol, may reach 80% or even 100% in certain countries such as Brazil. Consequently, it is important to be quite confident that with such a great diversity of fuels, the barrier effect of the fuel tanks remains sufficient to comply with the international environmental standards.

With this objective, predictions were made for a film of 5 layers HDPE/Binder/EVOH/Binder/HDPE with respective thicknesses of 2400/100/100/100/1000 in microns for each of the layers. The compositions of the model mixtures of fuels are those based on the ethanol tie line, i.e. on models of essence with increasing ethanol contents by volume, varying from 0 to 100%, and equal-volume proportions of iso-octane and toluene.

Figure 11:
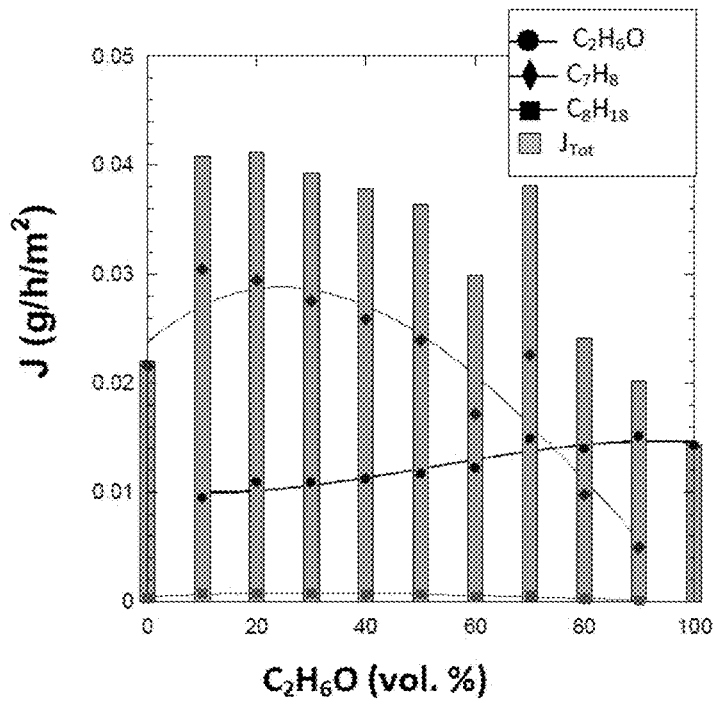

FIG. 11 makes it possible to evaluate the influence of the composition of this model essence on the partial fluxes and total fluxes $J_{Tot}$.

Regarding the partial fluxes, regardless of the ethanol content of the essence investigated, the flow of iso-octane is always much less than the flows of the other two solvents and does not show significant variation over the range of compositions studied. As for the ethanol flow, it is almost constant up to an ethanol content of 50%, then it increases slightly for mixtures even richer in alcohol. Here, the role of the upstream layer of HDPE therefore appears to be very important for limiting the flow of this polar compound. Finally, the compound by far the most affected by a change in composition of the model essence is toluene. FIG. 11 shows that the toluene flow passes through a maximum for a low ethanol content (about 10%) and then decreases strongly when the content of alcohol increases. The maximum observed, which cannot correspond to a decrease in toluene content when the ethanol content increases, is very probably connected with an effect of plasticization of the layer of EVOH by the ethanol. Beyond this maximum, the effect of plasticization by ethanol is more than compensated by the decrease in toluene content and the toluene flow then generally decreases considerably.

If we are interested in the overall permeabilities, they remain low for the two extreme compositions (0% and 100% ethanol). However, on adding just 10% of ethanol to the essence, the overall permeability is almost doubled because of the decrease in the barrier effect of the layer of EVOH, and then it remains at a quasi-stable level (about 0.04 g/h/m²) for a wide range of composition. In conclusion, according to the results from the simulation, the presence of ethanol may degrade the barrier performance of HDPE/Binder/EVOH/Binder/HDPE multilayer film, but the degradation remains limited to an increase in permeability by a factor close to 2.

Example No. 6: Influence of the Structure of the Multilayer Film

A final study considered the influence of the arrangement of the layers, with the objective of being able to optimize the arrangement of the different layers to give the lowest possible permeabilities. Until now, the multilayer structures tested, in industry or in the laboratory, have nearly all had the same structure, with two layers of HDPE on the sides and a layer of EVOH in the middle. For purposes of comparison, the fluxes were calculated for a reversed arrangement of the different layers.

The film studied therefore is made up of 5 layers EVOH/Binder/HDPE/Binder/EVOH, with respective thicknesses of each of the layers of 50/100/500/100/50 in microns, the permeability of which was simulated for a model mixture of fuels ethanol/iso-octane/toluene with composition by volume 20/40/40. It should be noted that this arrangement of the different layers does not seem realistic for industrial application notably owing to the high sensitivity of EVOH to moisture. Nevertheless, investigation of this arrangement can provide a comparison with the reversed arrangement that is widely used in industry. The results of this comparison are summarized in Table I.

TABLE I

| | $J_{C2H6O}$ (g/h/m²) | $J_{C8H18}$ (g/h/m²) | $J_{C7H8}$ (g/h/m²) | $J_{Total}$ (g/h/m²) |
|---|---|---|---|---|
| HDPE/B/EVOH/B/HDPE (250/100/100/100/250 μm) | 0.1435 | 0.0043 | 0.1042 | 0.2520 |
| EVOH/B/HDPE/B/EVOH (50/100/500/100/50 μm) | 0.2946 | 0.0020 | 0.0617 | 0.3583 |

Comparing the two multilayer structures having inverted arrangements but the same thickness for each layer, the overall permeability is increased by 40% when EVOH is placed on the two outer sides owing to a partial flux of ethanol about twice as high. However, this multilayer structure with the reversed arrangement offers a better barrier effect with respect to hydrocarbons.

The method of modeling according to embodiments of the disclosure therefore makes it possible to predict all of the partial fluxes of the various solvents (ethanol, iso-octane and toluene) through multilayer structures that are made up of several layers of polymers of different natures and thicknesses. Moreover, the method makes it possible to optimize on the one hand the thickness of the different layers of the structure and on the other hand the order of stacking of the materials constituting the different layers of the multilayer structure. Thus, tank structures can be modeled quickly based on these calculations, for best compliance with the environmental standards.

Finally, this method of modeling is advantageously carried out by means of a computer program, comprising program code instructions for executing the steps of the method, the program itself being executed by a processor.

The invention claimed is:

1. A method for pre-selecting or screening for a multilayer polymer structure with n monolayers (n≥2) having desired barrier properties against permeation of mixtures of solvents, said method comprising:
   1) selecting several initial compositions of solvent mixture E1 to Ey, each composition of solvent mixture comprising a mixture of at least two compounds selected from an oxygen-containing compound (a), an aliphatic compound (b) and an aromatic compound (c), in various proportions,
   2) for each composition of solvent mixture E1 to Ey, carrying out the following steps:
      a. for each monolayer included in the constitution of the multilayer structure, carrying out:
         a sorption measurement consisting of measuring an amount of each compound (a, b, c), of said composition of solvent mixture, absorbed by said monolayer, thus obtaining a model corresponding to the thermodynamic law of sorption of said layer,
         measurement of diffusion, by measuring partial fluxes, of each compound (a, b, c) of said composition of solvent mixture through said monolayer, thus obtaining a model corresponding to the kinetic law of diffusion of said layer,
      b. discretizing said multilayer structure in space and time, the discretization in space consisting of cutting up, virtually, each monolayer of the multilayer structure into X elementary slices, and then regarding said multilayer structure with n monolayers as a succession of (n−1) bilayers, each bilayer comprising an upstream monolayer A and a downstream monolayer B,
      c. based on the data measured for each monolayer in step 2.a:
         c.1. estimating partial fluxes (Ji) of each of the compounds (a,b,c) of said composition of solvent mixture between each elementary slice of said multilayer structure,
         c.2. at the interface between each upstream monolayer A and downstream monolayer B of said multilayer structure, estimating on the one hand a maximal sorption ceiling of said downstream monolayer B and on the other hand the composition of solvent mixture at inlet of said downstream monolayer B, said composition being limited to said estimated maximal sorption ceiling,
         c.3. performing a mass balance from slice to slice as a function of time, so as to obtain a concentration profile of each compound of said composition of solvent mixture in said multilayer structure as a function of time,
         c.4. adjusting the profile of concentrations, the profile of partial fluxes and the thicknesses of the elementary slices, taking into account monodirectional swelling of the structure,
         c.5. repeating steps c1 to c4 until the partial fluxes are conservative at every point of the structure,
      d. once the partial fluxes are conservative, selecting a multilayer polymer structure with n monolayers (n≥2) having the desired barrier properties.

2. The method as claimed in claim 1, wherein the solvent mixture is an essence comprising a mixture of at least two compounds selected from an oxygen-containing compound (a), an aliphatic compound (b) and an aromatic compound (c), in various proportions.

3. The method as claimed in claim 2, wherein the essence comprises a mixture of at least one oxygen-containing compound (a), an aliphatic compound (b) and an aromatic compound (c), in various proportions.

4. The method as claimed in claim 1, wherein prior to step 2c.1. for estimating the partial fluxes, an initialization step consists of calculating, from the values of sorption at inlet and outlet of the multilayer structure, corresponding activities of each of the compounds of said composition of solvent mixture at inlet and outlet of said structure, and then creating a linear activity profile for each of the solvents from inlet to outlet of the structure and then, based on this activity profile, estimating local concentrations (Ci) of each of the compounds of said composition of solvent mixture in each slice of said multilayer structure, as well as the thickness of the elementary slices, taking into account monodirectional swelling of said multilayer structure.

5. The method as claimed in claim 1, wherein step 2c.1. of estimating the partial fluxes consists of estimating on the one hand diffusion fluxes, from the local concentrations of each of the compounds of said composition of solvent mixture in each elementary slice, and on the other hand convection fluxes, from the partial fluxes measured in step 2a and the local concentrations of each of the compounds of said composition of solvent mixture in each elementary slice.

6. The method as claimed in claim 1, wherein the treatment at the interface between two monolayers of polymer materials different from step 2c.2 is based on the fact that there is equality of the flows between two adjacent monolayers and that the concentration of each of the compounds at inlet of the downstream monolayer B cannot exceed the sorption ceiling.

7. The method as claimed in claim 1, wherein the sorption ceiling is calculated from the activities of each of the compounds of said composition of solvent mixture, on the assumption that there is continuity of activity between the last slice of an upstream monolayer A overlapping with a first slice of a downstream monolayer B.

8. The method as claimed in claim 1, wherein each solvent mixture composition E1 to Ey comprises a proportion by volume (%) of one of the compounds (a) that varies from one composition to another, whereas the other compounds (b, c) have an identical proportion by volume.

9. The method as claimed in claim 1, wherein the number of solvent mixture compositions is between 5 and 10.

10. The method as claimed in claim 1, wherein each solvent mixture composition comprises a mixture of several compounds (a, b, c) selected from ethanol (a), iso-octane (b), and toluene (c).

11. A non-transitory medium comprising a computer program comprising program code instructions for executing the steps of the method of modeling as claimed in claim 1, wherein said program is configured to be executed by a processor.

* * * * *